(12) United States Patent
Tetzlaff (10) Patent No.: US 6,556,963 B1
(45) Date of Patent: *Apr. 29, 2003

(54) USER STATE SENSITIVE SYSTEM AND METHOD FOR NUTRIENT ANALYSIS USING NATURAL LANGUAGE INTERFACE

(75) Inventor: Linda S. Tetzlaff, Mt. Kisco, NY (US)

(73) Assignee: International Business Machines Corporation, Armonk, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/936,796

(22) Filed: Sep. 24, 1997

(51) Int. Cl.[7] .................. G06F 17/27; G06F 17/00; G06F 15/00
(52) U.S. Cl. .................. 704/9; 235/375; 600/300
(58) Field of Search .................. 704/1, 7, 9, 10, 704/275; 128/291, 630, 921; 434/238, 127; 600/300; 235/375

(56) References Cited

U.S. PATENT DOCUMENTS

| | | | | |
|---|---|---|---|---|
| 4,321,674 A | * | 3/1982 | Krames et al. | 364/413 |
| 4,686,624 A | * | 8/1987 | Blum et al. | 364/415 |
| 4,688,195 A | * | 8/1987 | Thompson et al. | 704/1 |
| 4,855,945 A | * | 8/1989 | Sakai | 364/413.29 |
| 5,233,520 A | * | 8/1993 | Kretsch | 364/413.29 |
| 5,282,265 A | * | 1/1994 | Rohra Suda et al. | 704/9 |
| 5,418,948 A | * | 5/1995 | Turtle | 704/9 |
| 5,478,989 A | * | 12/1995 | Shepley | 235/375 |
| 5,673,691 A | * | 10/1997 | Abrams et al. | 128/630 |
| 5,704,350 A | * | 1/1998 | William, III | 128/630 |
| 5,748,974 A | * | 5/1998 | Johnson | 704/9 |
| 5,805,775 A | * | 9/1998 | Eberman et al. | 704/257 |
| 5,819,735 A | * | 10/1998 | Mansfield et al. | 128/630 |
| 5,841,115 A | * | 11/1998 | Sheplay | 235/375 |
| 5,884,249 A | * | 3/1999 | Namba et al. | 704/9 |
| 5,960,384 A | * | 9/1999 | Brash | 704/9 |

* cited by examiner

*Primary Examiner*—Patrick N. Edouard
(74) *Attorney, Agent, or Firm*—Whitham, Curtis & Christofferson, P.C.; Louis J. Percello (57) ABSTRACT

An easy to use system and method personalizes dynamic nutritional requirements of a user. A natural language user interface is used to input information to a nutrient analysis system that integrates nutritional guidelines from diverse sources. A user of the system describes elements of a meal that she has either eaten or is considering eating, and the system responds with dynamic, personalized, state-sensitive feedback about the nutrient components of her choices in relation to her personal nutritional objectives.

10 Claims, 7 Drawing Sheets

USER STATE SENSITIVE SYSTEM AND METHOD FOR NUTRIENT ANALYSIS USING NATURAL LANGUAGE INTERFACE

BACKGROUND OF THE INVENTION

1. Field of the Invention

The present invention generally relates to the field of rule based computer systems and, more particularly, to a rule based system for nutrient analysis that uses a natural language interface.

2. Background Description

Many prior art systems, rely on menu selection for food specification. Menu selection is an effective and appropriate input mechanism when the user is unlikely to know or recall the item to be selected. However, in the case of food about to be eaten or food previously eaten, the user will simply know what is to be input, and may be encumbered by the overhead of menu navigation.

Because entries in the U.S. Department of Agriculture (USDA) nutrient database are cryptically and eccentrically described, considerable manual processing is required to extract useful values for consumer use. Other food selection systems and food databases are typically organized for browsing alphabetically or alphabetically within a single category (fruits and vegetables, meats, dairy, etc.), impeding search on complex descriptors. With these systems, users have limited choice in their description of amounts, being restricted to such specifications as grams, ounces and serving.

Many of the prior art systems are inflexible. Nutrient guidelines are from a single source, such as the USDA recommended daily amount (RDA), or a particular diet plan. However, any given user may require that considerations for different nutrients may come from a variety of sources. Some may be based on medical prescription, others on institutional guidelines, such as the American Cancer Society or the American Heart Association and still others on personal preference.

Many prior art systems make only limited and inflexible use of user state in the determination of targets; i.e., prior art systems are not directed to a specific user's requirements. For instance, many prior art systems do not account for a recent change in a user's exercise program, individual medical conditions like insulin dose with respect to user blood sugar, dynamic changes in nutrition requirements due to physical conditions like pregnancy, etc.

Previous systems require co-residence of code and data input on the same computer system. This means that an expensive and inconveniently heavy device is necessary to run the application or, alternatively, that there may be a significant delay in the entry of diet information.

SUMMARY OF THE INVENTION

It is therefore an object of the invention to provide an easy to use system and method for personalizing dynamic nutritional requirements of a user.

It is another object of the invention to provide an improved natural language user interface for a nutrient analysis system.

It is a further object of the invention to provide an improved nutrient analysis system that integrates nutritional guidelines from diverse sources.

According to the invention, a natural language food analyzer process is implemented in a multimedia computer system. A user of the system describes elements of a meal that she has either eaten or is considering eating. Using appropriate input and output devices, such as a keyboard, mouse, and/or microphone, she informs the system of her choices using either spoken or written natural language, and the system responds with dynamic, personalized, state-sensitive feedback about the nutrient components of her choices in relation to her personal nutritional objectives. Meal elements may also be uploaded from another computer or personal data assistant.

The food analyzer recognizes the individual words in the input stream by invoking an appropriate a word or speech recognizer, depending on whether the input is typed or spoken. The task of the recognizer is to disambiguate and resolve unknown or multiply determined words based on a speech model. The amended (disambiguated and resolved) input is passed to a input parser which decomposes it into canonical representations of quantity and food, using the language model. A fuzzy logic search engine does searches against the food model to locate the specified food and return its nutrient values. The fuzzy logic search engine generates both exact and approximate matches. The resulting food descriptor is passed to a feedback generator which analyzes its components with respect to a user model containing personalized nutritional objectives, and rule-based descriptors of a diet protocol and provides immediate, contextualized feedback to the user based on the input.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
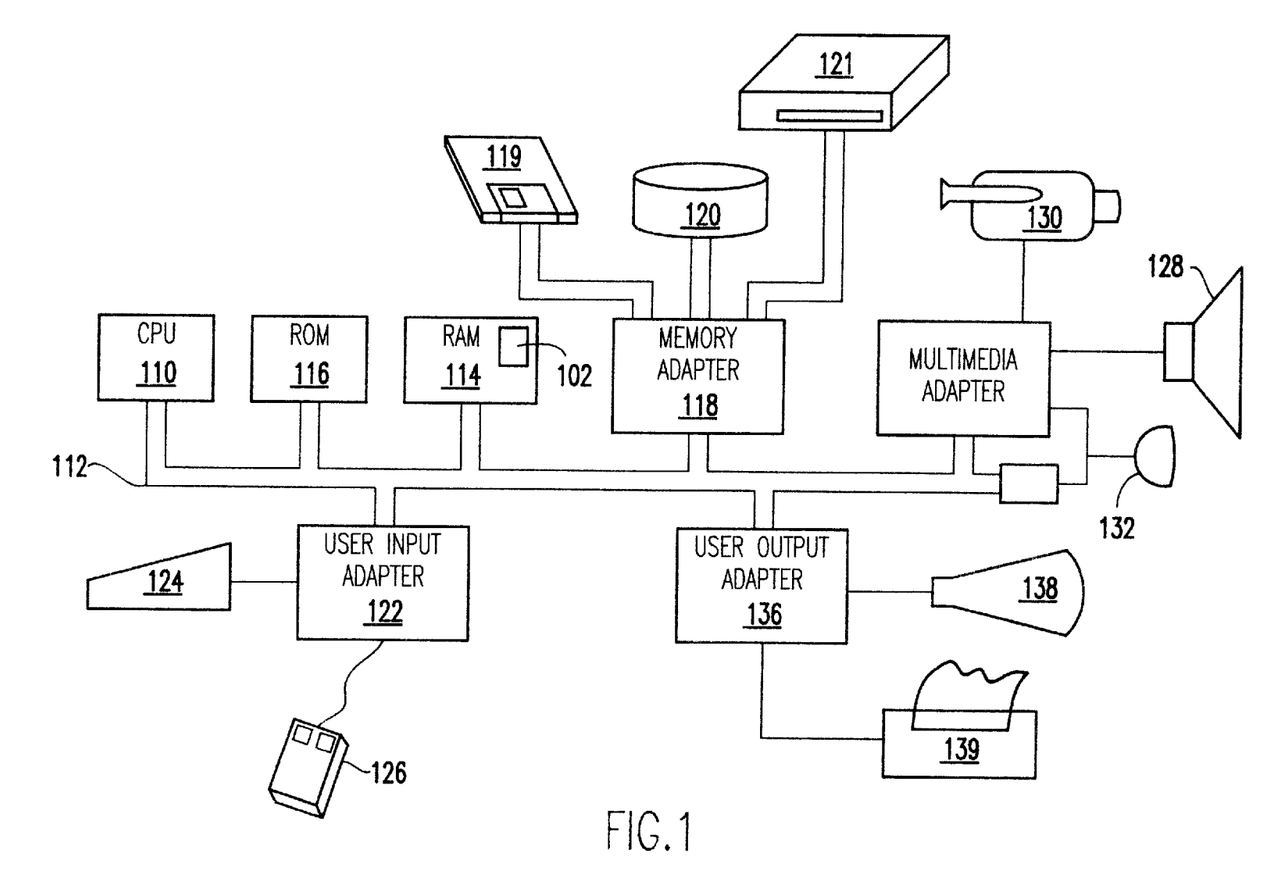
FIG. 1 is a block diagram of a preferred computer system of the type on which the present invention may be implemented.

Referring now to the drawings, and more particularly to FIG. 1, there is shown an example of a general purpose computer system 100, such as an IBM Personal Computer (PC), on which a preferred embodiment of the present invention may be implemented. Components in the computer system 100 are connected by and communicate over a system bus 112. A Central Processing Unit (CPU) 110, Read Only Memory (ROM) 116, and Random Access Memory (RAM) 114 typically are connected to the system bus 112. The preferred embodiment includes one or more application programs 102, shown here as residing in RAM. Additional memory, e.g., diskettes 119, hard disks 120, and compact disc ROM (CD-ROM) 121, can be connected to the system bus 112 by appropriate memory adaptors 118. Input/output (I/O) adaptors 122, 136 connect devices to the system bus 112 that interact with a user. For example, a keyboard 124 and/or mouse 126 input are connected to the system bus 112 through an appropriate user input adapter 122, and a display 138 and/or printer 139 are connected to the system bus 113 through an appropriate user output adapter 136. Multimedia functions can be added to the system 100 by using an appropriate multimedia adapter 134. Such multimedia adapters are used to input and output audio signals through audio input devices, for example, a microphone 132, and audio output devices, for example, one or more loud speakers 128. Video input, for example, through a camera 130, and video output, through display 138, are also enabled by multimedia adaptors. Speech recognition is accomplished by using an appropriate adapter 175, such as the IBM Voice-Type Dictation Adapter.

Figure 2:
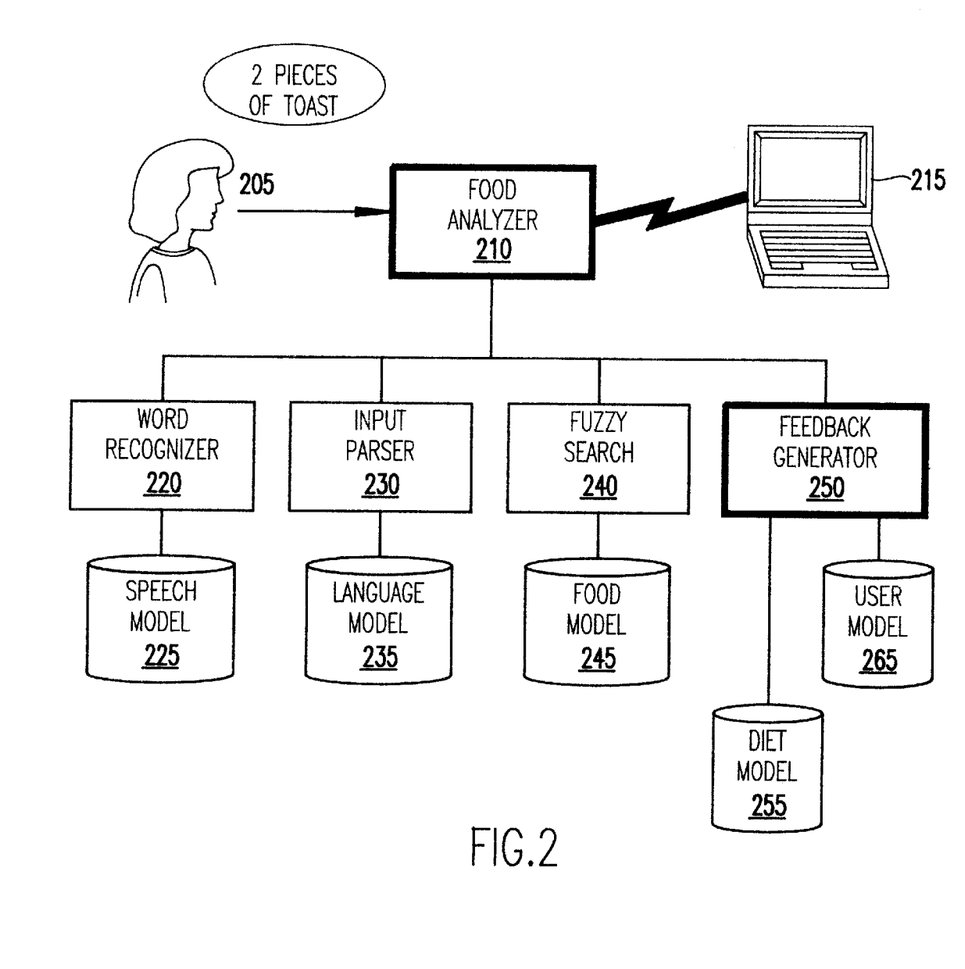
FIG. 2 is a block diagram of the architecture of the nutrient analysis system according to the invention.

FIG. 2 is a block diagram illustrating a preferred embodiment of a natural language food analyzer process, one of the applications 102 residing in RAM in the system shown in FIG. 1. A user 205 of the system describes elements of a meal that she has either eaten or is considering eating. Using the appropriate input and output devices described above (e.g., keyboard, mouse, microphone), she informs the system of her choices using either spoken or written natural language, and the system responds with dynamic, personalized, state-sensitive feedback about the nutrient components of her choices in relation to her personal nutritional objectives. Meal elements may also be uploaded from another computer or personal data assistant 215.

A food analyzer 210, explained in more detail below, receives the user's natural language input or input from the computer or personal data assistant 215. The food analyzer 210 is the driver program for the food analyzer. Its first task is to recognize the individual words in the input stream. This is accomplished by invoking an appropriate and available word or speech recognizer 220, depending on whether the input is typed or spoken. Such recognizers and the dictionaries they use are well known in the data processing arts.

The task of the recognizer 220 is to disambiguate and resolve unknown or multiply determined words based on a speech model 225. The amended (disambiguated and resolved) input is passed to an input parser 230 which decomposes it into canonical representations of quantity and food, using the language model 235, described below. Input parsers are also well known in the data processing arts. One preferred parser is the C Parser/Translator (CPT) developed by David Johnson of IBM Research. A fuzzy logic search engine 240 does searches against the food model 245 using known search engines to locate the specified food and return its nutrient values. The fuzzy logic search generates both exact and approximate matches. The resulting food descriptor is passed to a feedback generator 250 which analyzes its components with respect to a user model 265 containing personalized nutritional objectives and rule-based descriptors of a diet protocol 255 and provides immediate, contextualized feedback to the user 205 based on the input.

Table 1 describes a language model 235 used as input to the input parser 230 (for example, David Johnson's C Parser/Translator).

TABLE 1

| Quantity | Size Modifier | Unit | Food Modifier | Food |
|---|---|---|---|---|
| 1 | large | slice | pepperoni | pizza |
| 12 | | ounce | diet | soda |

The language model 235 describes the canonical form of a food item, consisting of a quantity, a size modifier, a unit, a food modifier and a food item. Quantity may include integer, fractional or decimal numbers or number ranges, or non-numeric quantifiers such as "a" or "some". The size modifier is a qualitative size descriptor such as small, medium or large. Food units may be represented by standard names, such as "tablespoon", "piece", "cup" or "ounce", or by colloquialisms, such as "to taste". The food modifiers are functionally adjectival and may be used to differentiate individual foods within a food group. Examples include trade names, such as "Smucker's", or generic descriptions, such as "pepperoni", "semi-sweet". Food items are functionally nominal. Examples include: "strawberry jam", pizza, milk, and chocolate. Table 1 shows possible parsings for the following examples:

1. a large slice of pepperoni pizza, and
2. a 12 oz can of diet coke.

It is assumed that the language parser will make arithmetic conversions when possible (e.g., a=1; 2 12 oz cans=24 oz). If not, they will be made in the food model.

Figure 3:
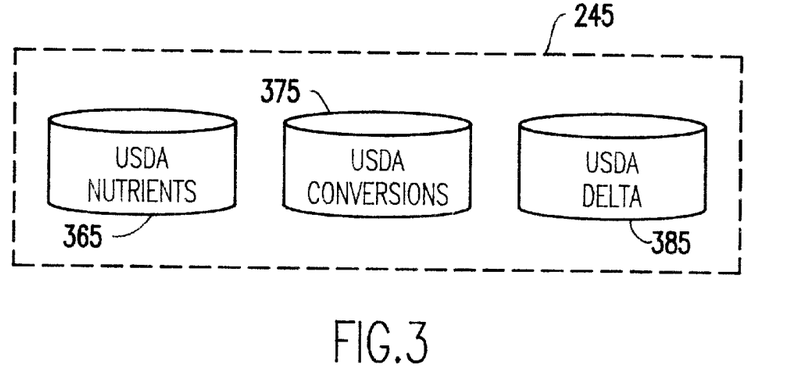
FIG. 3 is a block diagram illustrating elements of the food model database used by the nutrient analysis system shown in FIG. 2.

Food model 245 is the source of nutrient component analysis. The food model is derived from databases provided by the USDA. As shown in FIG. 3, the USDA supplies a nutrient database 365, which is a list of foods and their nutrient components. A second database 375 provides a secondary source of serving size to gram equivalents for each of the foods in the nutrient database. The food names in the USDA databases are processed, by a language processor 230 in FIG. 2 to produce entries in the style of the language model 235, which are then loaded into the food model 245. This results in a new database with food, food modifier, size modifier and unit as described for the language model 235.

In addition to the grams per serving field, the various nutrient components such as calories, carbohydrates, fats, vitamin C, etc., are extracted from the USDA database 365. Each of the nutrient fields represents the quantity found per 100 grams of food.

Some foods may be represented by more than one serving descriptor. These are carried in the second USDA database 375 shown in FIG. 3, and are processed to create a second database extension in the food model.

The food and food modifier field pairs will exactly match pairs in the base represented by Table 2 but will contain new size modifier, unit and grams per serving relations.

In addition to the entries supplied by the USDA, entries may be supplied by a user. These are maintained separately in a database 385 shown in FIG. 3 so that they can be merged into a processed USDA file, should the originals be updated.

Figure 4:
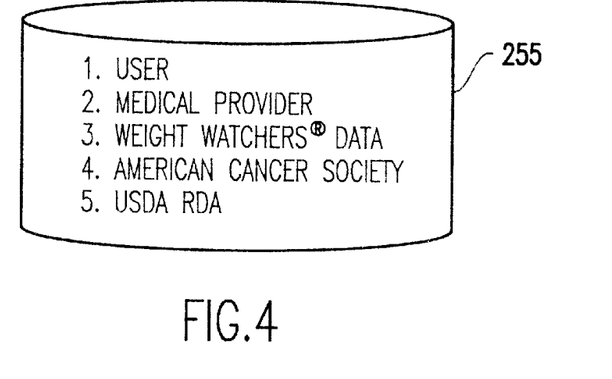
FIG. 4 is a block diagram illustrating the. diet model database used by the nutrient analysis system shown in FIG. 2.

Table 4 and FIG. 4 illustrate the diet model 255 of FIG. 2 which is used to determine the target values for each nutrient, and the appropriate actions for the user to take under specified conditions.

TABLE 4

| Nutrient | Floor | Ceiling | Rules |
|---|---|---|---|
| Vitamin C | 100 | | |
| Fat | | fat × 9 < .1 kcal | |
| Carbohydrate | | breakfast = 20 | carb > ceiling |
| | | lunch = 30 | then insulin = insulin + 10 |
| | | dinner = 30 | |

For each nutrient, there may be specified a floor value, i.e., the daily minimum requirement, a ceiling value, i.e., the value which daily consumption should not exceed, and a collection of rules describing actions to be taken in the event of certain specified conditions. For example, the USDA RDA for Vitamin C is 100 mg/day. This would be specified as "Vitamin C, floor=100". If the diet were to target a maximum of 10% fat, this could be specified as "fat, ceiling fat×9=0.1 kilo calories". If carbohydrates exceeded the meal target and a diabetic were to need additional insulin, this could be specified as "carbohydrate, ceiling breakfast=20, lunch=30, dinner=30, case if carbs>ceiling, then insulin= insulin+10. The nutrient name is the same as the name the food model 245. The floor and ceiling expressions may be decomposed into components such as breakfast, lunch, etc., and may reference other nutrients in the model. The rules case is also an expression. Case expressions may reference other nutrients in the diet model 255 or variables in the user model 265 shown in FIG. 2.

The diet model 255, shown in more detail in FIG. 4, is composed of an ordered list of files each of which may specify rules for one or more nutrients. This enables flexible specification of nutrient target values from multiple sources. This is useful as it is often the case that a particular source only concerns itself with a selected set of nutrients. For example, the user may have a personal objective to make sure she or he is getting enough fiber for digestive comfort. The provider may need to regulate carbohydrates and insulin because the user is diabetic. The user may be using a Weight Watchers® program to help manage weight. The American Cancer Society may publish guidelines for current prophylactic nutrient levels for cancer prevention. At the same time the user wants to make sure she or he is at least meeting the USDA RDA requirements for vitamins and minerals. The rules for these various guidelines could be independently specified and/or packaged and searched in priority order or other rules or strategies could be developed for conflict resolution.

The combination of the rule based specification of the diet plan coupled with the flexible organization of the rule sets enables descriptive development of any manner of diet plan with little or no development of additional code.

Tables 5 and 6 illustrate the user model 265 which is used to tailor information and actions to a particular user. Table 5 contains information about stable user characteristics, and Table 6 contains the user's current state.

TABLE 5

| Variable | Value |
|---|---|
| sex | F |
| diabetes | type 2 |
| allergies | peanuts, grass |

TABLE 6

| Date | Time | Variable | Value |
|---|---|---|---|
| 01/01/97 | 06:00 | weight | 150 |
| 01/01/97 | 07:00 | blood glucose | 120 |
| 01/01/97 | 07:30 | meal | breakfast |

Figure 5:
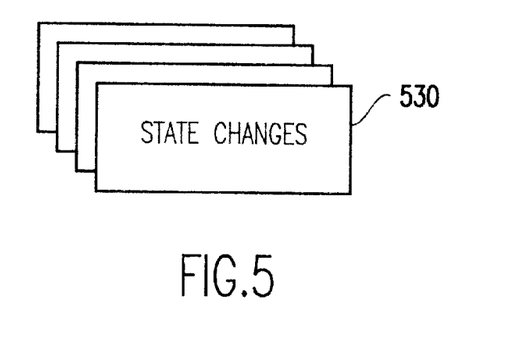
FIG. 5 is a block diagram illustrating the history files developed in the user model database used by the nutrient analysis system shown in FIG. 2.

As shown in FIG. 5, a state history 530 is developed from state changes. The user characteristics are contained in an attribute file as represented by Table 5. For each attribute, there is an attribute name field and an attribute value field. Examples of relevant stable attributes include, but are not restricted to, sex, medical conditions such as diabetes or high blood pressure and allergies. The current state reflects attributes or events which change over time and which are relevant to program processing. For each state variable there is a field reflecting the current date and time at which the data was collected, the variable name and its value. Examples of typical states include, but are not restricted to, weight, blood glucose and meal. Finally, the user model includes a history, shown in FIG. 5, which contains a running log of each change in a state variable.

Figure 6:
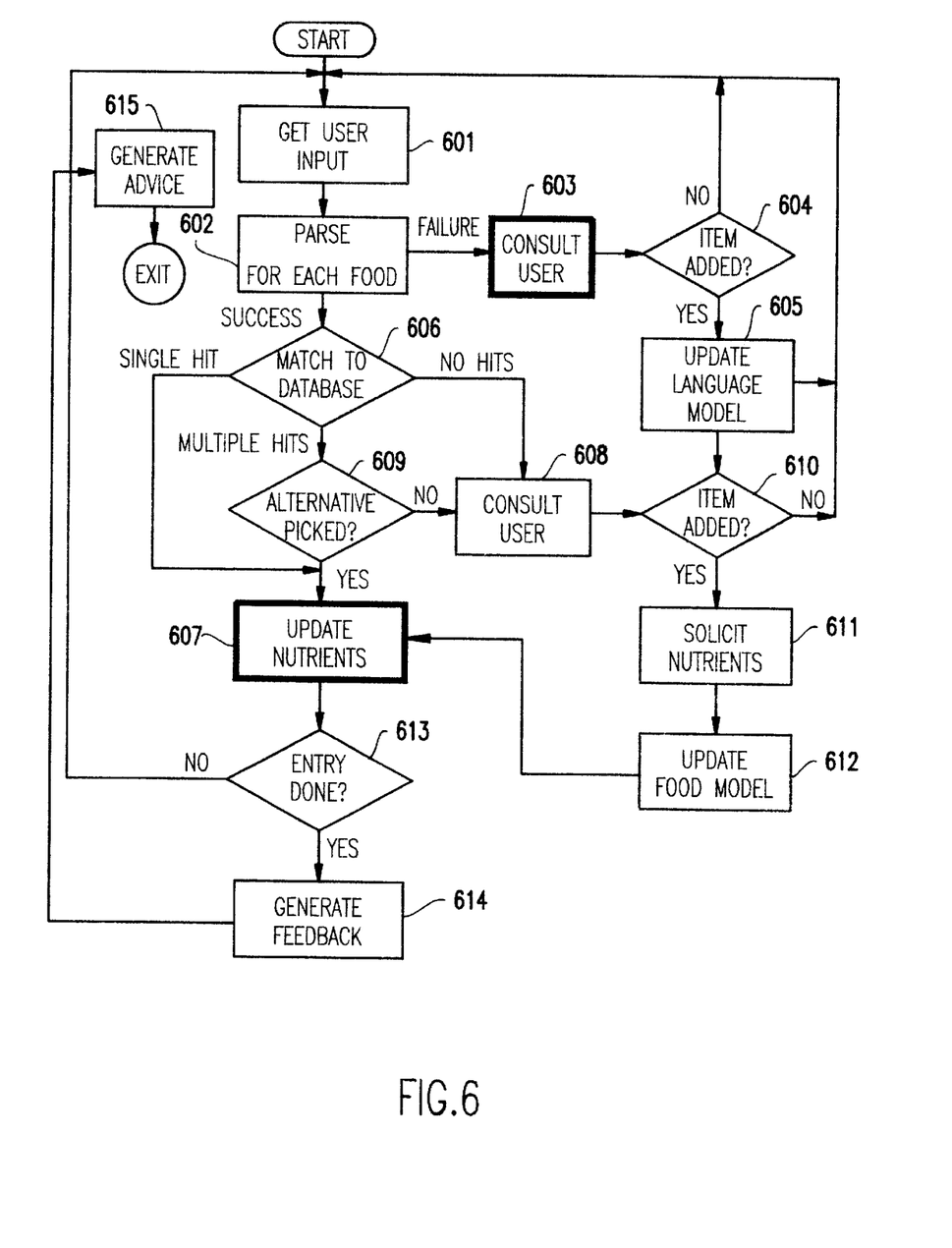
FIG. 6 is a flow diagram showing the steps performed by the food analyzer method according to the invention.

FIG. 6 shows the control flow of the food analyzer 210. The first step in function block 601 retrieves the user input and makes sure that the components of the user input are understood. This is done using standard system I/O and the word recognizer 220 shown in FIG. 2. User input is in the form of natural language. For example, it may consist of one food (e.g., an egg) or a list of foods (e.g., two slices of bacon and an egg). It is necessary to decompose each food into a computable form, which is done in function block 602 (using the parser 230 ) by parsing the input against the language model 235, shown in FIG. 2. If the food does not appear in the language model 235, then a "consult the user" step in function block 603 is performed to determine whether or not the unrecognized food should be added to the language model. The user is prompted in decision block 604 to determine if the user wants to add the item. If the user does not want to add the item or phrase to the language model, then a new input is solicited in function block 601. If the user wishes to add the item, then the language model 235 is updated in function block 605.

If the food is recognized by the language model, then the fuzzy search engine 240 searches in comparison block 606 to match the canonical representation of the food to the food model 245. If a single hit is obtained, then the nutrient values are computed and updated in function block 607 in the dict model 255, as described in more detail below. If there are no hits, then the food analyzer process 210 prompts the user in function block 608 to determine if the user would like to add the entry to the food model 245. If there are multiple hits, the food analyzer process 210 displays the alter natives and prompts the user to pick one of the displayed alternatives in decision block 609. If the user does not select one of the items displayed, then the food analyzer process 210 prompts the user in function block 608 to determine if the user would like to add the entry to the food model 245.

If the user would like to add the entry to the food model, as determined in decision block 610, then food analyzer 210 solicits the relevant nutrient data in function block 611, updates the food model in function block 612, and proceeds to update the running nutrient totals in function block 607.

If the user input at function block 601 is a component of a list of foods provided by the user, or an element of a recipe as determined in decision block 613, the next item in the list is obtained by getting the next user input. Otherwise, the appropriate feedback is generated in function block 614, as described in below in the feedback generator 250 description. The generated feedback is displayed in function block 615 before the process exits.

Figure 7:
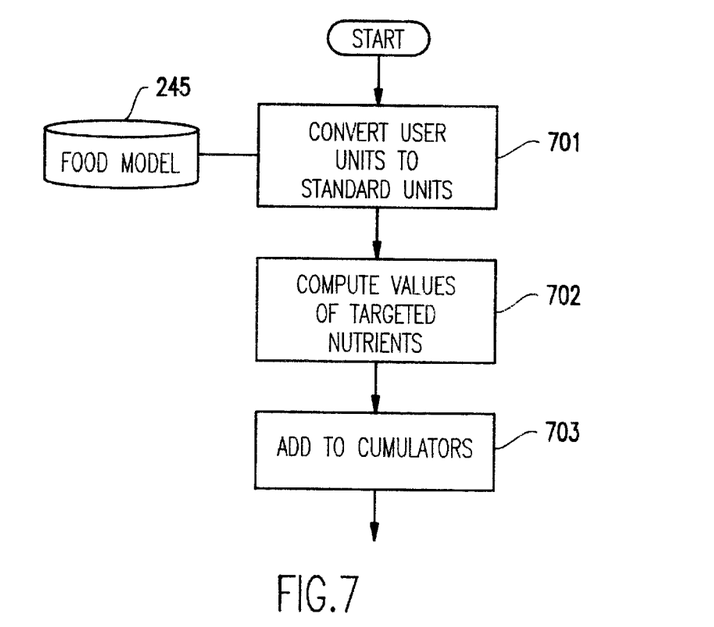
FIG. 7 is a flow diagram showing the steps performed by the nutrient processor of the food analyzer shown in FIG. 6.

FIG. 7 describes the control flow of the nutrient processor that performs the "update nutrients" step in function block 607 of FIG. 6. The nutrient processor takes the canonical description of the user's food item (e.g., 2 slices of whole wheat bread) and a record in the food model 245 for 1 slice of whole wheat bread, converts the canonical description into standard units, and computes the number of grams in the user's food item in function block 701. In this example, the food model 245 record contains grams per slice, and nutrients per 100 g for whole wheat bread. The number of grams eaten is divided by 100 and multiplied by each of the target nutrient values (e.g., carbohydrates, fat, salt) to get the nutrient values for the food item in function block 702. These values are added to the running total for the meal in function block 703.

Figure 8:
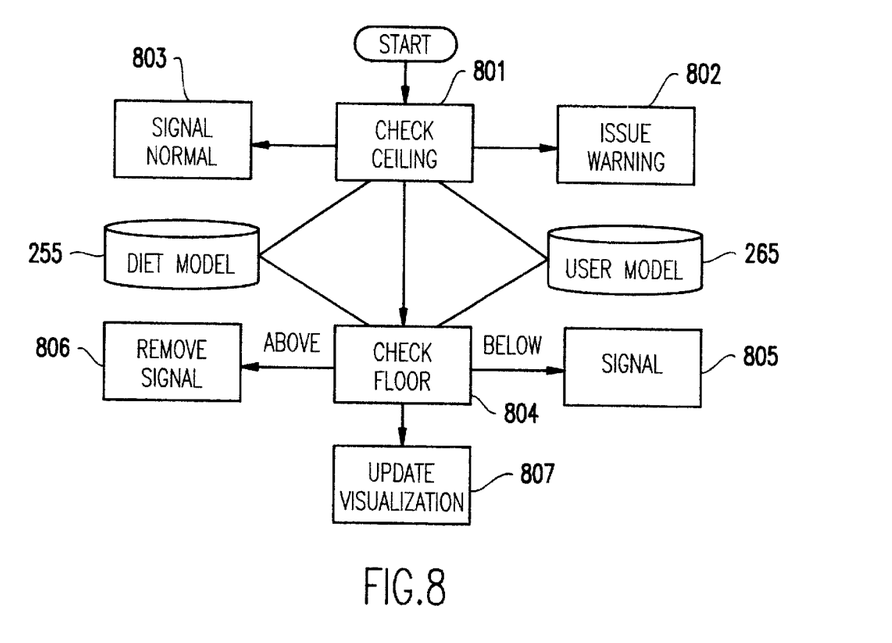
FIG. 8 is a flow diagram showing the steps performed by the feedback generator used by the food analyzer shown in FIG. 6.

FIG. 8 illustrates the control flow of the feedback generator 250. The first task is to check the accumulated value of the nutrient against the expression defining the target maximum value in function block 801 from the diet model 255 and the user model 265. If the maximum is exceeded, a warning is issued in function block 802. If the user is still (or again) below the maximum, it must make sure that the display is in a "normal" state without a warning in function block 803. Similarly, the accumulated value of the nutrient is compared to the expression defining the minimal value in function block 804. If the accumulated value is below the floor, a warning is issued in function block 805. If it is above the floor a "normal" display is restored in function block 806. The accumulated value of the nutrient is displayed using some appropriate visualization in function block 807, such as a slider, an animation or other informative graphic, providing the context of the nutrient targets.

Figure 9:
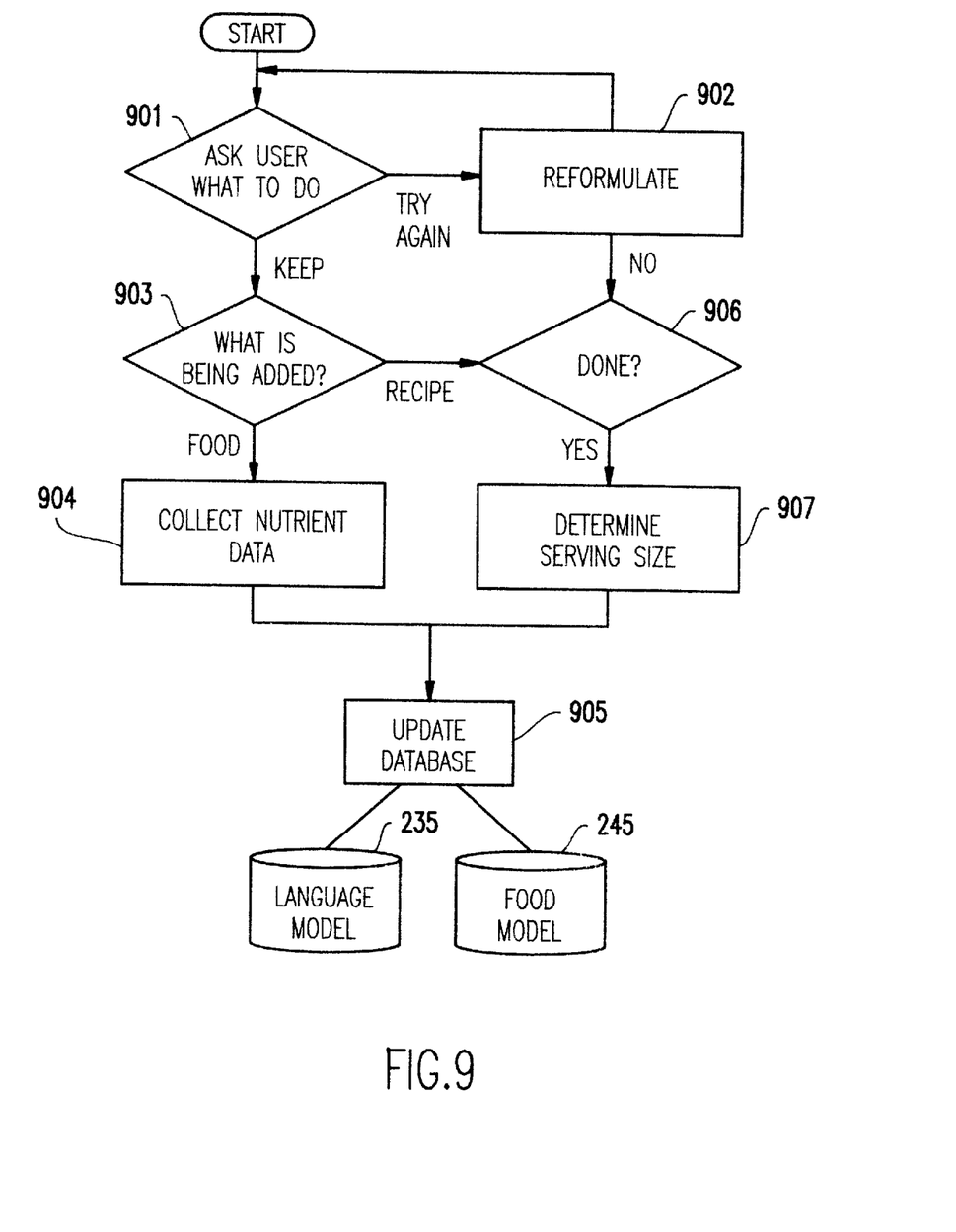
FIG. 9 is a flow diagram showing the steps performed by the user consultant used by the food analyzer shown in FIG. 6.

FIG. 9 illustrates a user consultant process that performs step of function block 603 shown in FIG. 6. A number of conditions may prevent the food analyzer from locating a particular food item. For example, the grammar describing the food may not apply, the food may not be known to the parser's dictionary, or the food may not match anything in the food model. In any event, the user needs to make a decision in function block 901 about whether to treat the entry as a mistake, in which case the user should reformulate her or his entry in function block 902, or whether it should be treated as a new food value. If it is a new food entry it could be a basic food, or it could be a component of a recipe or user shorthand for some frequently eaten group of foods. This is determined in function block 903. If it is a basic food, the user is asked for the nutrient data in function block 904, and the language model 235 and/or the food model 245 are updated in function block 905. If the entry is an element of a recipe and the recipe is compete as determined in decision block 906, the user is asked for the serving size in function block 907. The nutrient data is computed in function block 905 from the food model 245, and the language model 235 and the food model 245 are updated. If the recipe has not yet been fully specified, the next food item is solicited from the user.

Figure 10:
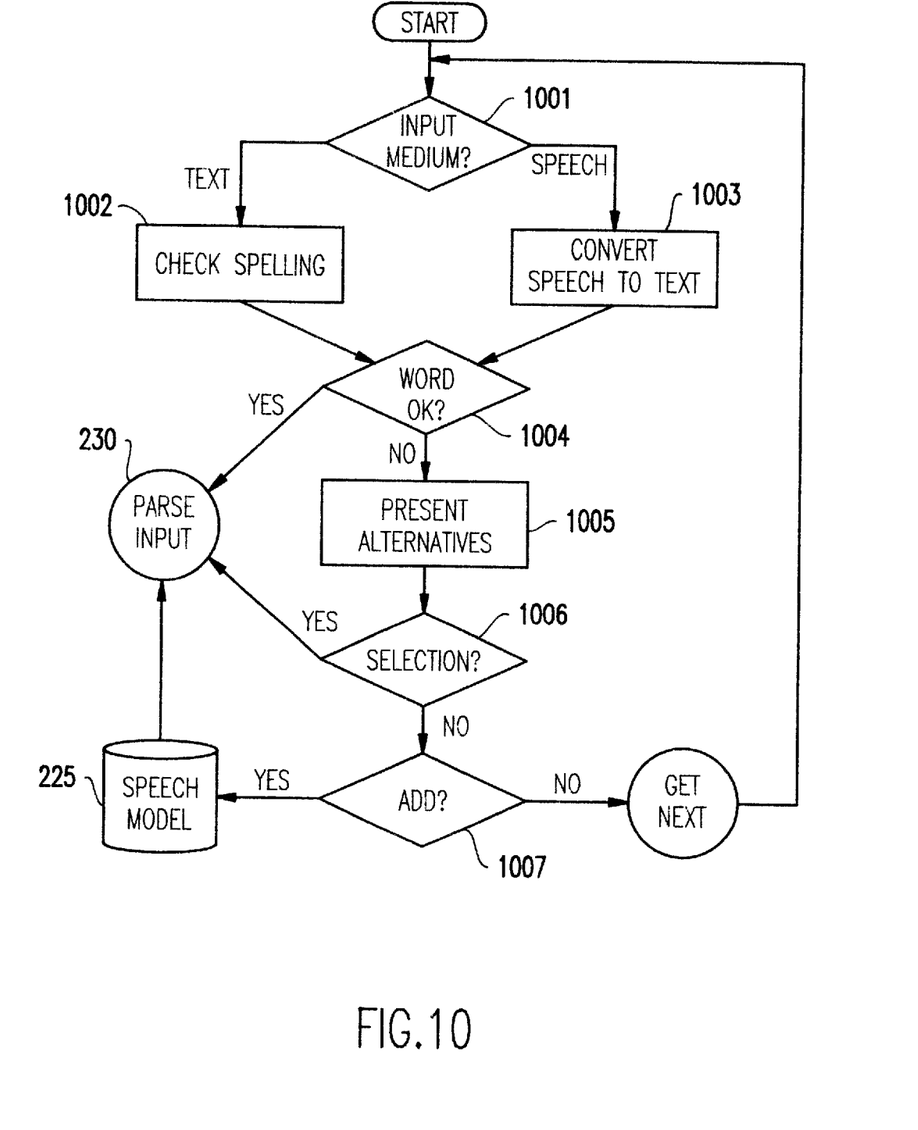
FIG. 10 is a flow diagram showing the steps performed by the word recognizer used by the food analyzer shown in FIG. 6.

FIG. 10 illustrates the control flow of a word recognizer 220 shown in FIG. 2. The word recognizer first determines in decision block 1001 whether the input is text or speech. If text, the word recoginizer checks its speech model 225 in function block 1002 to see if it recognizes the word, using a (forgiving) text dictionary. If speech, the spoken words are converted to text in function block 1003 by a speech recognizer. In either case, a determination is made in decision block 1004 as to whether the word is valid. If the word is valid, it returns it to the food analyzer 210 which then invokes the parser 230. If it is not valid, the user is presented with a list of possible alternatives in function block 1005. If the user selects one of these alternatives in decision block 1006, it is returned to the food analyzer 210 which then invokes the parser 230. If no alternative is selected, if the user wants to add a word as determined in decision block 1007, the word is added to the speech model 225. Then control is returned to the food analyzer 210. If the user does not want to incorporate the word, the food analyzer goes on to the next input 1001.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A nutrient analysis system comprising:
   a natural language food processor for receiving a natural language input from a user, wherein the natural language input describes food and is input other than by a displayed menu selection;
   an input parser that uses a language model to parse the natural language input into food components;
   a speech recognition system coupled to the natural language processor to record meals and other food intake events;
   a first database accessed by the natural language processor, said database being a model of the speech used to specify food selection;
   a second database storing a food model;
   a fuzzy logic search engine that searches the food model in the second database using a canonical description of a food which consists of a quantity, a size modifier, a unit, a food modifier and a food, to generate one or more hits, wherein said food model is updated with input from a user to accommodate new foods, new food names and nutrient requirements;
   a feedback generator that produces one or more running totals for one or more nutrients in the hits; and
   a third database accessed by the feedback generator, said database describing a state of the user as it relates to the user's nutrient intake, the state of the user including static attributes, current state and a state history, wherein said third database stores a set of rules corresponding to a predetermined diet plan for a user, and wherein the feedback generator compares the food described in said natural language input with said set of rules.

2. The nutrient analysis system recited in claim 1 wherein the input parser utilizes a canonical set of descriptive rules conforming to rules of natural language.

3. The nutrient analysis system recited in claim 1 further comprising a database of rules accessed by the search engine, said database storing a natural language description of eaten food.

4. The nutrient analysis system recited in claim 3 wherein said database of rules decodes the USDA nutrient database names.

5. The nutrient analysis system recited in claim 4 wherein a multiplicity of nutrient target values are extracted from a multiplicity of sources in a predetermined order.

6. The nutrient analysis system recited in claim 4 wherein a multiplicity of sources are presented to said user and said user selects a source from among said multiplicity of sources.

7. The nutrient analysis system recited in claim 1, wherein said third database stores information indicative of at least one of a state of the user as it relates to the user's nutrient intake, the state of the user including static attributes, current state and a state history.

8. The nutrient analysis system recited in claim 1 wherein said natural language input specifies a unit of size of said food.

9. The nutrient analysis system recited in claim 8, wherein said unit of size is a non-numeric unit of size.

10. The nutrient analysis system recited in claim 1, wherein said feedback generator provides an indication of whether the food satisfies said diet plan.

\* \* \* \* \*